US008859452B2

(12) United States Patent
Zhang et al.

(10) Patent No.: US 8,859,452 B2
(45) Date of Patent: Oct. 14, 2014

(54) METAL CYANIDE COMPLEX CATALYST AND ITS PREPARATION AND APPLICATION

(75) Inventors: Xinghong Zhang, Hangzhou (CN); Guorong Qi, Hangzhou (CN); Binyang Du, Hangzhou (CN); Renjian Wei, Hangzhou (CN); Xueke Sun, Hangzhou (CN)

(73) Assignee: Zhejiang University, Hangzhou, Zhejiang Province (CN)

( * ) Notice: Subject to any disclaimer, the term of this patent is extended or adjusted under 35 U.S.C. 154(b) by 289 days.

(21) Appl. No.: 13/394,267

(22) PCT Filed: Dec. 13, 2010

(86) PCT No.: PCT/CN2010/079735
§ 371 (c)(1),
(2), (4) Date: Mar. 5, 2012

(87) PCT Pub. No.: WO2012/019405
PCT Pub. Date: Feb. 16, 2012

(65) Prior Publication Data
US 2012/0172566 A1 Jul. 5, 2012

(30) Foreign Application Priority Data

Aug. 13, 2010 (CN) .......................... 2010 1 0253928
Aug. 13, 2010 (CN) .......................... 2010 1 0253936

(51) Int. Cl.
*B01J 27/26* (2006.01)
*B01J 27/25* (2006.01)
(Continued)

(52) U.S. Cl.
CPC ................ *C08G 63/82* (2013.01); *C08G 64/34* (2013.01); *C08G 65/2663* (2013.01); *C07F* (Continued)

(58) Field of Classification Search
CPC ....................................................... B01J 31/22

USPC .................................. 502/175, 201, 217, 224
See application file for complete search history.

(56) References Cited

U.S. PATENT DOCUMENTS 4,500,704 A   2/1985   Kruper, Jr. et al.
4,826,053 A   5/1989   Keller
(Continued)

FOREIGN PATENT DOCUMENTS

CN        1740208 A        3/2006
CN     101003622 A         7/2007
(Continued)

OTHER PUBLICATIONS

Sun, Xueke, et al., Alternating Copolymerization of Carbon Dioxide and Cyclohexene Oxide Catalyzed by Silicon Dioxide/Zn-ColII Double Metal Cyanide Complex Hybrid Catalysts with a Nanolamellar Structure, Journal of Polymer Science: Part A: Polymer Chemistry, vol. 46, 2008, pp. 3128-3139.

*Primary Examiner* — Duc Truong
(74) *Attorney, Agent, or Firm* — Jacobson Holman PLLC; Jiwen Chen (57) ABSTRACT

A metal cyanide complex catalyst and its preparation and application are disclosed. The formula of this catalyst is $M^1_a[M^2(CN)_b L1_c]_d(X)_m(L2)_n \cdot xSu \cdot yL3 \cdot zH_2O$ and its preparation method comprises: (A) adjusting pH of a mixed solution I' of L3, $M^3_e[M^2(CN)_b L1_c]_f$, de-ionized water I, alcohol and/or ether solvent to less than 7.0, and adding it into a mixed solution II' of $M^1(X)_g$ salt, Su or Su precursor, de-ionized water II, stirring for reaction under 20° C.-120° C. for 0.5-200 hours, separating and drying to obtain a solid product; and (B) repeatedly dispersing the solid into an anhydrous organic solvent containing L2 to form a slurry, distilling, separating and drying to obtain the metal cyanide complex catalyst. The catalyst is useful in preparing polyethers, polycarbonates and polyesters by homopolymerization of epoxides, or copolymerization of epoxides with carbon dioxide or anhydrides.

7 Claims, 3 Drawing Sheets

(51) Int. Cl.
*C08G 64/34* (2006.01)
*C08G 65/26* (2006.01)
*C07F 15/06* (2006.01)
*C08G 63/82* (2006.01)
*C08G 63/42* (2006.01)
*B01J 27/06* (2006.01)
*B01J 27/053* (2006.01)

(52) U.S. Cl.
CPC ....... 15/065 (2013.01); *C08G 63/42* (2013.01)
USPC ............ 502/175; 502/201; 502/217; 502/224

(56) References Cited

U.S. PATENT DOCUMENTS

| | | | |
|---|---|---|---|
| 6,362,126 | B1 | 3/2002 | Grosch et al. |
| 6,713,599 | B1 | 3/2004 | Hinz et al. |
| 6,762,278 | B2 | 7/2004 | Hinz et al. |

FOREIGN PATENT DOCUMENTS

| | | |
|---|---|---|
| CN | 101151296 A | 3/2008 |
| CN | 101511909 A | 8/2009 |
| CN | 101942081 A | 1/2011 |

METAL CYANIDE COMPLEX CATALYST AND ITS PREPARATION AND APPLICATION

This is a U.S. national stage application of PCT Application No. PCT/CN2010/079735 under 35 U.S.C. 371, filed Dec. 13, 2010 in Chinese, claiming the priority benefits of Chinese Application No. 201010253928.2, filed Aug. 13, 2010 and Chinese Application No. 201010253936.7, filed Aug. 13, 2010, which are hereby incorporated by reference.

TECHNICAL FIELD

The present invention belongs to the field of catalysts used for polymer synthesis, and in particular involves a metal cyanide complex catalyst and its preparation method as well as applications.

BACKGROUND OF THE INVENTION

Polyether, polycarbonate, polyester and poly(ester-carbonate) are important functional polymer materials that can be prepared from epoxides homopolymerization, copolymerization of epoxides with monomers such as $CO_2$ or anhydride. Among these materials, polycarbonate, polyester and poly(ester-carbonate) are new kind of degradable polymer materials and their monomers such as $CO_2$ and anhydrides are abundant and inexpensive. Therefore, these materials have very significant development promises. The key issue for synthesizing these (bio) degradable polymers is to obtain complete alternative copolymers.

Especially, for aliphatic polycarbonates (APCs), which are produced by the copolymerization of $CO_2$ and epoxides, the key characteristics of their application are their biodegradability and oxygen barrier properties. These properties are mainly determined by whether the molecular structure of the copolymer is completely alternating. According to current technology, heterogeneous catalysts such as zinc glutarate catalyst and rare earth metal ternary catalyst system could catalyze the full alternating copolymerization of $CO_2$ and epoxides. However, they exhibited very low productivity. Usually, the best catalyzing activity is about 60 g copolymer/g catalyst. Because of the low activity and a large amount of the required catalyst, it is difficult to separate the catalyst from the product, which causes high production cost. On the other hand, when homogeneous catalysts such as zinc bis (β-diiminates) catalyst, or Salen-Co catalyst are employed as catalysts for the $CO_2$-epoxides copolymerization, complete alternating copolymer are achieved successfully with an activity of above 100 g polymer/g catalyst (up to about 900 g polymer/g catalyst). However, these homogeneous catalysts require expensive raw materials, long and strict synthetic route, rigorous reaction condition, as well as the difficulty in separating the catalysts from reactive products.

Traditional double metal cyanide (DMC) complex is an efficient catalyst for epoxides homopolymerization to produce polyether polyols, which presents the advantages of very low unsaturation degree (0.005~0.008 mol/kg) and narrow molecular weight distribution ($M_w/M_n$<1.2), and thus is clearly better than those polyols made by using KOH catalyst. However, due to the DMC catalyst's high activity, which usually results in fast polymerization and strong exothermal effect in a short reaction time after the induction stage, such catalyst may lead to the generation of products with high molecular weight and process serious danger during polymerization. As a result, ensuing a smooth progression of the catalyzing process and eliminating high molecular weight end products are the keys to obtain high quality polyols.

In recent years, the high activity of the DMC catalysts also attracted researchers to use them in the reactions for the copolymerization of $CO_2$ and epoxides to produce polycarbonate and the copolymerization of $CO_2$ and anhydride to produce polyester. Very regrettably, there are various drawbacks in current technology using DMC to catalyze the copolymerization of epoxides and $CO_2$. These drawbacks mainly include the resultant polymer containing a significant portion of polyether, low carbonate units, and a relatively high content of cyclic carbonate byproduct. This is because the generation of polyether and cyclic carbonate are thermodynamically favorable. The current published DMC catalysts catalyzes propylene oxide (PO)/$CO_2$ copolymerization to obtain poly(ether-carbonate)s with a low molecular weight or a low glass transition temperature. The product's thermal characteristics, such as glass transition temperature ($T_g$), and the thermal decomposition temperature ($T_d$) were also unsatisfied. Moreover, massive production of cyclic carbonate byproduct caused waste of propylene oxide monomers and complexity in post-reaction processing.

According to current technology, such as those methods reported in Chinese Patent Application No. 200680010849.0 and No. 200780027326.1, DMC catalysts were used for making poly(ether-carbonate). The structure of the polymerization products includes a significant amount of polyether. The polymerization products contain a significant amount of cyclic byproducts and the molecular weight is low. The DMC catalyst disclosed by No. 200680010849.0 showed a polymerization activity of about 0.8 kg polymer/g catalyst at the highest.

Moreover, U.S. Pat. No. 4,500,704 discloses that a Zn—Co double metal complex catalyst with 2-methoxyethanol as a complexing agent was used to catalyze PO—$CO_2$ copolymerization under 700 psi polymerization pressure and at 35° C. for 48 h. The resultant polymer showed a high molecular weight of 23000. However, its glass transition temperature $T_g$ was only 8° C., suggesting that the carbonate chain units content was rather low (complete alternating PO/$CO_2$ copolymerization products with a high molecular weight MW exhibit a $T_g$>35° C.). In addition, the technologies of using double metal cyanide catalyst to catalyze $CO_2$ copolymerization disclosed in U.S. Pat. No. 6,713,599, U.S. Pat. No. 6,762,278 and U.S. Pat. No. 4,826,053 have the same problems. That is, the products have low molecular weights; the weight percentage of polycarbonate is generally lower than 20 wt. %; a high cyclic carbonate content in the products as well as a low catalyst productivity.

From the perspective of the catalysis principle, the catalytic performance of the heterogeneous DMC catalyst is internally determined by the structure of the active site and externally influenced by the specific surface area of the catalyst. The current technology mainly improves DMC catalyst through alternation of the external complexing agents, addition of salt and a supporter. These methods are usually processed in water, thus usable organic external complexing agents are limited. Most oil-soluble organic solvents are difficult to form strong or weak coordination structure with active metals in the water phase, and in fact it is difficult to substantially modify the environment and the coordination structure of the active sites. Thus, the catalyst performance of the catalyst made from the current technology was not significantly improved for epoxides-$CO_2$ copolymerization compared to traditional DMC catalysts. In conclusion, it is really an unsolved challenge for a DMC catalyst to catalyze $CO_2$-epoxides copolymerization to achieve full alternating polycarbonate with a high molecular weight, high productivity, high selectivity and low cyclic carbonate byproducts.

SUMMARY OF THE INVENTION

The present invention relates to a metal cyanide complex catalyst and its preparation and application. This catalyst is different from the traditional DMC catalyst in catalyst composition, structure and active site. It is of a nano-lamellar or nano-spherical shape and nano-hole structure with high specific surface area. Especially, it exhibits excellent catalytic performance for the epoxides-$CO_2$ copolymerization.

A typical metal cyanide complex catalyst has the following formula:

$$M^1{}_a[M^2(CN)_bL1_c]_d(X)_m(L2)_n \cdot xSu \cdot yL3 \cdot zH_2O \qquad (1)$$

wherein, $M^1$ is a divalent metal ion, which is preferably selected from $Zn^{2+}$, $Co^{2+}$, $Ni^{2+}$ or $Fe^{2+}$;

$M^2$ is a divalent or trivalent metal ion (not including $Fe^2$ or $Fe^{3+}$), which is preferably selected from $Co^{3+}$, $Ni^{2o}$, $Cd^{2+}$, $Cr^{3+}$ or $Mn^{3+}$;

L1 is an internal ligand which coordinates with $M^2$ and can be a ligand well known in the field. It is preferably selected from the group consisting of mono-dentate ligands with O, S, P or N as coordinate atom, bi-dentate ligands with O, S, P or N as coordinate atom and halide anions or a mixture of one or two of them. Preferably, it is usually selected from the group consisting of $Cl^-$, $Br^-$, $I^-$, $CN^-$, $N_3{}^-$, $OCN^-$, $SCN^-$, $OH^-$, $NH_3$, pyridine or bipyridine.

X is an anion, and preferably selected from the group consisting of $F^-$, $Cl^-$, $Br^-$, $I^-$, $OAc^-$, $SO_4{}^{2-}$, $NO_3{}^-$, aryloxy anions, organic carboxylic ions and a mixture of one or more of them, more preferably, X is selected from the group consisting of $Cl^-$, $Br^-$, $I^-$, $OAc^-$, $SO_4{}^{2-}$, $NO_3{}^-$, aryloxy anion and organic acid ions.

L2 is an electron-donating neutral ligand well known in the field that coordinates with $M^1$. Preferably, L2 is a neutral ligand with N, O, P and S as coordinated atom, and more preferably, L2 is selected from the group consisting of N-alkyl imidazole, N-aryl imidazole, bipyridine, pyridine, aliphatic nitriles, aromatic nitriles, N,N'-dialkyl amide, N,N'-diaryl amide, N-substituted cyclic amide, sulfoxide or sulfone compounds, organic carboxylates, ketones, cyclic ketones, phosphates, all alkyl-substituted cyclotriphosphazene, full-aryl-substituted cyclotriphosphazene, carbonates, lactones, thioether, cyclic carbonates or cyclic ethers.

It should be noted that L2 is an electron-donating neutral ligand. Especially, L2 cannot be proton-containing organic ligands such as alcohols, carboxylic acids, phenols and corresponding macromolecules.

Su is selected from one or more of the IIA and IIIA group metal elements, including halides, sulfates, nitrates, lithium halide salt, silicon dioxide, or titanium dioxide. When Su contains silicon dioxide or titanium dioxide, these oxides are in situ generated with the production of the catalyst. Thus, it could be recognized as an inert carrier for the catalyst. The preparation method was disclosed in detail in a Chinese Patent Application No. ZL200710066763.6 (Publication number: CN101003622) by the present inventors.

L3 is a water-soluble polymer, a polymer that can self-assembly in a mixed solution of water and alcohol, or in a mixed solution of water and ether, or in a mixed solution of water, alcohol and ether. Preferably, L3 is selected from the group consisting of polyethylene oxide polyols, and the following polymers that is water soluble or can self-assembly in the mixed solutions of water/alcohol, water/ether and water/alcohol/ether: diblock or triblock copolymer of ethylene oxide and propylene oxide, polyester, poly(ether-ester), poly-ether-modified polysiloxanes, polyhydroxyethyl (meth)acrylate, poly-N,N'-diethyl acrylamide, poly-N-isopropylacrylamide, poly(ethylene oxide)-b-poly(N,N'-diethyl acrylamide)s, poly(ethylene oxide)-b-poly(N-isopropylacrylamide)s, poly(ethylene oxide)-b-poly(acrylic acid)s, poly(ethylene oxide)-b-polymethacrylates, or one or more of them. During the preparation of the catalyst, L3 can either act as an external complexing agent or an effective template for regulating the micro-structural shape and pore structure of the catalyst. Consequently, L3 can form nano-aggregate via self-assembly in water or the mixed solution of water, alcohol and ether. This is the key factor to the formation of the nano-sheet or spherical shape and porous structure in aggregation physics of the catalyst. These structural characteristics are one of the characteristics that distinguish the catalysts provided by the present invention from other DMC catalysts.

It is noted that a and d are positive numbers, b is positive integer, c is 0, 1 or 2, m and n are positive numbers, x, y and z are zero or positive numbers, and a:d=1~4, a:n=0.001~5.

From chemistry point of view, metal ion $M^1$ in $M^1{}_a[M^2(CN)_bL1_c]_d(X)_m(L2)_n$ can strongly coordinate with cyanide anion $[M^2(CN)_bL1_c]$ or coordinate with L2. L2 cannot be removed by strong drying in vacuum, suggesting the bond of L2 and the active site is stronger than that of traditional physical adsorption. However, it is known that tertiary butyl alcohol in the catalysts that were prepared with tertiary butyl alcohol as the complexing agent can be removed completely by strong vacuum drying. Besides, L2 is also difficult to be washed out by alcohols and ethers whose electron-donating capability is weaker than L2. The infrared spectrum, wide-angle X-ray diffraction and laser Raman spectrum of these catalysts also suggest that L2 linked to metal $M^1$ via coordination. Due to such new active site as the key reason, the catalyst disclosed in the present invention achieved unprecedented catalytic performance.

The process for preparing the above metal cyanide complex catalysts, comprise the following steps:

Step 1: a solution I' was prepared by mixing the cyanide metal salt of formula (2) with L3, de-ionized water I, alcohol and/or ether solvents, and then the pH value of the solution I' was adjusted to less than 7.0. A solution II' was prepared by mixing $M^1(X)_g$ salt, Su or Su precursors, and de-ionized water II. Then solution I' and solution II' were mixed by adding solution I' into solution II' to react with each other at 0~120° C. for 0.5~200 h while being agitated. The preferable reaction time was 1-60 h, and the preferable reaction temperature was 20-100° C. The agitation speed was 100-2000 r/min through mechanical or magnetic stirring. After reaction, the resultant solid precipitate was separated by centrifugation and dried in the air.

$$M^3{}_e[M^2(CN)_bL1_c]_f \qquad (2)$$

wherein, $M^3$ is an alkali metal ion, alkali earth metal ion or hydrogen ion, e and f are positive numbers, $M^2$, L1, b, and c are the same as (1) described before, wherein, L3, $M^1$, X and Su are the same as (1) described before, g is 1 or 2, In the mixed solution I', the molar ratio of the cyanide metal salt of formula (2) and de-ionized water I is 0.005~2 g/mL, preferably, is 0.1~1 g/mL.

In the mixed solution I', the weight ratio of L3 and de-ionized water I is 0~40%.

In the mixed solution I', the volume fraction of alcohol (and/or ether) and the de-ionized water I is 0~2, preferably, 0~0.8. These solvents are helpful to enhance the dispersion and self-assembly of L3, which is the physical basis for forming a porous structure.

The alcohol solvents are well known alcohol in the field, preferably tertiary alcohols and secondary alcohols whose carbon atom number is less than 6. The ether solvents are well known ether in the field, preferably at least one of tetrahydrofuran, 1,4-dioxane, ethylene glycol dimethyl ether, propylene glycol dimethyl ether or crown ether, or a mixture of at least two of the above solvents.

The acids used to adjust the solution acidity may use inorganic acids and water-soluble organic acids. Preferably, the acid is selected from the group consisting of hydrochloric acid, nitric acid, sulphuric acid, phosphoric acid or carbonic acid. Dosage of the acid can at least ensure that the pH value of the solution is below 7, preferably, below 4. This can eliminate the possible alkaline structure in the catalyst (Zn—OH structure) and obtain proper range of the pH, which is also favorable to the dispersion and self-assembly of L3 in the solution.

In the mixed solution II", the molar ratio of $M^1(X)_g$ salt/de-ionized water II is 0.05~1 g/1 mL, preferably, 0.1-0.5/1 mL. The molar ratio of the cyanide metal salt of formula (2)/$M^1(X)_g$ salt is 1/1~50, preferably, 1/1~30. The mass ratio of the cyanide metal salt of formula (2) and Su (or Su precursor) is 1/0~20.

When Su is selected as the metal salts, preferably, it is selected from the group consisting of halides, sulfates and nitrates of the IIA and IIIA group metal elements, and lithium halide salt. The weight percentage of Su in the final catalyst is 0~10%. Such metal salts are expected to form more flaws on the catalyst surface and thus increase the numbers of the active sites on the catalyst surface.

When Su is $SiO_2$ or $TiO_2$, it can be recognized as an inert carrier of the catalyst, since it is produced in situ during the preparation of catalyst with silicon ester, titanium ester as precursors. The preparation method related to such catalyst was published in a Chinese Patent Application No. ZL200710066763.6 (Publication number: CN101003622) of the inventors of the present invention. However, a significant difference is that the present invention introduced L3, which leads to the formation of physical porous structure in the catalyst. In this case, the mass fraction of Su in the final catalyst is 5~90%.

Step 2: the solid product from step 1 is repeatedly dispersed and reslurried in an anhydrous organic solvent containing L2. The molar ratio of L2/the cyanide metal salt of formula (2) is 0.1~10. The treat temperature is 20~120° C., preferably, 40~100° C., or the reaction can be processed in a refluxing temperature; the reaction time is 0.5~200 h, preferably, 1-48 h. The slurry process occurs under an inert atmosphere or in a closed reactive vessel. After dispersion and slurry process, the metal cyanide complex catalyst is obtained by a further separation process, including distillation, centrifugation or filtration, and then dried to a constant weight.

In a preferred preparation method, $M^1(X)_g$ salt is added into the anhydrous organic solvent containing L2. The molar ratio of $M^1(X)_g$ salt/the cyanide metal salt of formula (2) is 0~2. When $M^1(X)_g$ salt is added, it is expected to increase $M^1$ metal ion content in the catalyst. At least, it is expected to guarantee no weight loss of $M^1$ metal ion in step II, and consequently enhance the amounts of active site in the catalyst.

In step 2, all organic solvents are well-known and common alcohols or ethers. The alcohol is selected from the group consisting of tertiary alcohol and secondary alcohol whose number of carbon atoms is less than 6, the ether is selected from at least one of the group consisting of tetrahydrofuran, 1,4-dioxane, ethylene glycol dimethyl ether, propylene glycol dimethyl ether, crown ether and a mixture thereof. These organic solvents are not only complexing agents for preparing traditional DMC catalyst, but also good solvents for washing off L3. Excessive residual L3 in the catalyst is unfavorable to the dispersion of the catalyst and the diffusion of monomers to the active center during polymerization reaction. Sometimes, it may even prolong the induction period. However, a small amount of L3 usually exists in the catalyst. Moreover, the residue of these organic solvents (i.e.: alcohols and ethers with low boiling point) is proved to be no enhancement for the catalyst activity, although these solvents could influence the shape and size of the crystalline grain of the catalyst. Meanwhile, the residue solvents especially alcohols often result in the decrease of molecular weight due to the chain transfer reaction to these alcohols during polymerization. As a result, the synthesized catalyst should be dried sufficiently. The catalysts in this invention do not contain the aforesaid solvents (i.e.: alcohols and ethers with low boiling point), which is also a significant difference structurally compared to traditional DMC catalysts.

It is noted that previous DMC catalysts presented almost the same polycarbonate selectivity for epoxides-$CO_2$ copolymerization, although these catalysts had different catalyst activity. This phenomenon suggests that various existed preparation methods do not change the chemical structure and micro-environment related to the active site. While in this invention, an electron-donating complexing agent L2 was selected and coordinated with electron-deficient $M^1$ metal ion, and thus form an active component denoted as $M^1_a[M^2(CN)_b L1_c]_d(X)_m(L2)_n$. When this catalyst was performed to catalyze the copolymerization of epoxides and $CO_2$, it exhibited a significant improvement in the polycarbonate selectivity (alternative degree). In addition, it is demonstrated that the strategy of changing the polycarbonate selectivity by adjusting the structure of the active site of the DMC catalyst is successful.

In preparation method of metal cyanide complex catalysts provided by the present invention, during the slurry process of step 2 is also close to a solvothermal process due to low water content in the system. The experimental results indicate that this process could improve the coordination interaction between L2 and $M^1$. A better result can be achieved when the coordination ability of L2 and $M^1$ is greater than the solvation ability of $M^1$ with alcohols or ethers. A majority amount of L3 in the catalyst can be removed through the washing process of step 2. The remained L3 in the catalyst was proved to have no significant influences on the catalytic activity and selectivity but have effect on the pore size of catalyst, which led to the uncertainty of the induction period for the copolymerization. The drying process in step 2 is absolute and the small molecule such as tetrahydrofuran, tertiary butyl alcohol can be removed completely.

In the metal cyanide catalysts disclosed in this invention, the molar ratio of $M^1/M^2$ (i.e.: a/d) is 1~4, the molar ratio of $M^1/L2$ (i.e.: a/n) is 0.001~5. The SEM results show that it presented a nano-lamellar or spherical shape (see FIG. 1). The WAXD patterns show the catalyst was in polycrystalline. The widened diffraction peaks exhibit that the average size of these crystal grains was below 100 nm (see FIG. 2). The pore structure of catalyst was measured by BET method ($N_2$ absorption and desorption experiment). Before the test, the organic components such as L3 and L2 in the catalyst must be and are usually removed thoroughly for accurate determination of the surface area and pore size. Usually calcination method is used to get rid of organic components. Generally calcinations below 400° C. can get rid of the organic components without destroying the backbone of the catalyst. In addition, repeated extractions through strong polar solvents under 200° C. can get rid of the organic components. The pore structure of the catalysts can be accurately determined after processing. The experimental results show that the nano-pore structure was not regular, the average pore diameter was 3~100 nm, the surface area was 50~800 m$^2$/g, usually 100~600 m$^2$/g.

The metal cyanide catalysts prepared in this invention is highly active and selective for catalyzing homopolymerization of epoxides, $CO_2$ (or anhydride)-epoxides copolymerization to produce polyether, polycarbonate (or polyester) respectively.

It is a further object of the present invention to provide a method for using the metal cyanide complex catalyst of the present invention to catalyze epoxides homopolyrization for preparing polyether, catalyze epoxides alternating copolymerization with anhydride for preparing polyester, catalyze epoxides copolymerization with $CO_2$ for preparing polycarbonate, and catalyze epoxides terpolymerization with anhydride and $CO_2$ for preparing poly(ester-carbonate). The epoxides are well known compounds in the field and are selected from at least one of the group consisting of ethylene oxide, propylene oxide, butylene oxide, 1,1-dimethylethylene oxide, epichlorohydrin, epibromohydrin, styrene oxide, cyclohexene oxide, 4-vinyl cyclohexene oxide, cyclopentene oxide, α-alkylene oxides whose number of carbon atom is 5~20. Cyclic anhydride is also well known compound in the field and preferably is selected from maleic anhydride, glutaric anhydride, succinic anhydride, diglycolic anhydride, phthalic anhydride, or a mixture thereof.

When the metal cyanide complex catalysts in this invention are applied to catalyze epoxides ring-opening polymerization (ROP), it exhibits a high catalytic efficiency. In addition, this polymerization can proceed steadily without a strong exothermic process. As a result, the pressure and temperature of the reaction system can be steady and the activity of the catalyst can be maintained at a relatively long reaction time. Moreover, the tail peak at the side of high molecular weight part can be reduced.

Using the above metal cyanide complex catalyst for catalyzing the copolymerization of epoxides/cyclic anhydrides and the terpolymerization of epoxides/cyclic anhydrides/$CO_2$ exhibits high catalytic activity and the resultant copolymer has high alternating degree. These polymerizations are described as follows: The autoclave was firstly dried thoroughly by vacuum-$N_2$ cycle at high temperatures for removing trace water; then the catalyst, epoxides, and/or starting materials were put into the autoclave at room temperature, then the autoclave was sealed. For epoxides/anhydride copolymerization, the reaction pressure was the systematic pressure produced itself; for epoxides/cyclic anhydride/$CO_2$ terpolymerization, the reaction pressure was 0.5~10 MPa. The reaction temperature was 0~180° C., preferably, 20~150° C.; the reaction time was 0.5~100 h, preferably, 2~24 h. The starting materials are polyether polyols, polyester polyols, poly(ether-ester) polyols with various molecular weights and small molecule alcohols. The aforesaid polymerization can also proceed without adding starting materials. In this case, water in the reaction system is considered as a starting material. For the copolymerization of epoxides/anhydride, the catalyst productivity is more than 2 kg polymer/g active component, the copolymer selectivity is >95% and the number-average molecular weight is >10,000. For the terpolymerization of epoxides/anhydride/$CO_2$, the catalyst productivity is up to 1.5 kg polymer/g active component, the alternative degree is >95% and the number-average molecular weight is >20,000.

In particular, using the metal cyanide complex catalyst of the present invention can catalyze the alternative copolymerization of epoxides/$CO_2$ to synthesize aliphatic polycarbonates with high productivity and selectivity.

A method for preparing aliphatic polycarbonates using the metal cyanide complex catalyst of the present invention comprises the following steps: adding the metal cyanide complex catalyst of the present invention to an autoclave to catalyze the copolymerization of epoxides and $CO_2$. The reaction temperature is 20-150° C., $CO_2$ pressure is 0.5~10 MPa and reaction time is 1~48 h. The obtained crude products is purified and dried to obtain aliphatic polycarbonate. The weight ratio of the metal cyanide complex catalyst to epoxide is 1 g/1~100 kg.

According to this method, the reaction temperature is 20-150° C., preferably, 30-120° C. Too low reaction temperature will result in low epoxide's conversion and longer reaction time; while too high reaction temperature will significantly increase the polyether chains content in the resultant copolymer.

According to this method, the mentioned $CO_2$ pressure is 0.5~10 MPa, preferably, 1.5~8.0 MPa. Because the reaction occurs in a closed system and the system is processed into a vacuum prior to adding $CO_2$, the copolymerization reaction pressure is the $CO_2$ pressure. The experiment showed that: copolymerization under relatively low $CO_2$ pressure proceeded smoothly without significantly decreasing the catalyzation efficiency. However this caused a slight increase of the polyether chains content in the resultant copolymer. While under relatively high pressure, copolymerization proceeded smoothly with a decrease of the polyether chains content in the resultant copolymer to a certain degree. However, the investment in equipment increases. Therefore, the selected reaction temperature and $CO_2$ pressure in this invention are based on the comprehensive consideration of efficiency, cost and quality of the production.

In this invention, the mentioned copolymerization can be carried out in solution or bulk. When it is performed in solution, the available solvent is aliphatic cycloethers whose number of carbon atom is below 12, aliphatic ketones whose number of carbon atom is below 10, carbonate, cyclic carbonate, alkyl nitrile or alkyl benzene whose numbers of carbon atom are below 12, preferably, tetrahydrofuran, 1,4-dioxane, cyclohexanone, dimethyl carbonate, diethyl carbonate, propylene carbonate and or ethylene carbonate.

The purification of the crude products of epoxides-$CO_2$ copolymerization can be either distilled under a reduced pressure for removing unreacted monomer and/or organic solvent, or distilled after removing the catalyst via press filtration, or centrifugation firstly. Further purification for the products can be finished by the following steps: the product is dissolved into methylene dichloride or tetrahydrofuran, trace catalyst in the diluted product could be removed by simple centrifugation, and then precipitated in excess methanol or ethanol, dried under vacuum to a constant weight.

Active hydrogen-containing compounds can be used as the starting material for the copolymerization, preferably water, alcohols, phenols, acids, polyether polyols, polycarbonate polyols, poly(ether-ester) polyols and polyester polyols, its functionality is 1~8, number-average molecular weight is <10,000, the molar ratio of the functionality of the starting material/epoxide is 0~0.5, preferably, 0~0.01. When the molar ratio of the functionality of the starting material/epoxide is 0, means that no any starting materials are used. In order to reach the asserted effect of this invention, it should be careful to use starting materials, which act as a molecular weight regulator for the copolymerization. Theoretically speaking, too much starting materials will result in a decrease of molecular weight of the product.

Compared to the traditional double metal cyanide catalysts which are used for catalyzing the copolymerization of epoxides/$CO_2$ to prepare aliphatic poly (ether-carbonate), the significant effect of the catalyst of the present invention is that it can not only improve the copolymer molecular weight and selectivity dramatically but also keep a high productivity. The key factor for this significant catalytic performance is attributed to the metal cyanide complex catalyst of formula (1). This catalyst presents significant selectivity for the epoxides/$CO_2$ copolymerization and thus increases the degree of alternation.

The catalyst in this invention exhibits high productivity for preparing aliphatic polycarbonates. Generally, the productivity of the catalyst is >1.0 kg polymer/g catalyst, preferably, >1.5 kg polymer/g catalyst. It should be noted that the precondition of such high productivity of the catalyst is that the resultant copolymer is close to full alternating structure with the alternative degree >90%, preferably, >95%. Such high productivity of the catalyst is not for poly(ether-carbonate) with a low alternative degree. Currently, among the catalysts reported for the copolymerization of epoxides/$CO_2$, only salen-based cobalt complexes, zinc dicarboxylate catalysts and ternary rare earth metal catalysts can simultaneously obtain the copolymers with a high selectivity (alternative degree >90%, preferably, >95%) and weight-average molecular weight ($M_w$>80,000). However, the reported productivity of zinc dicarboxylate catalysts, ternary rare earth metal catalysts and Salen-based Cobalt complexes are 60, 60 and about 900 g polymer/g catalyst, respectively. The later complex is a homogeneous catalyst, and its preparation is complicated.

Moreover, the aliphatic polycarbonates via the catalysis of the mentioned catalyst of the present invention are provided. Using the aforementioned method to synthesize the aliphatic polycarbonates can achieve not only a high productivity, but also the following advantages at the same time: the weight-average molecular weight is >80,000, the molecular weight distribution is 1.2~4, alternative degree is >90%, in most case, >95%, the content of cyclic carbonate in the crude product is <10 wt %, usually <2 wt %. It is noted that the alternative degree of the copolymer is calculated by an equation: alternative degree=content of carbonate unit/(content of carbonate unit+content of ether unit). The contents of carbonate unit and ether unit in the copolymer are calculated from HNMR spectra. The molecular weight ($M_w$) and its distribution of the resultant copolymer are determined by gel permeation chromatography at 35° C. using tetrahydrofuran (THF) as a solvent, using mono-dispersed polystyrene as a standard calibration. The narrow PDI of the copolymer makes DMC catalyst in this invention better than zinc dicarboxylate catalysts and ternary rare earth metal catalysts. Significantly, a very low content of cyclic carbonate in the crude product reduces the use of units, the complexity of the after-treatment process and the production cost.

Meanwhile, the aliphatic polycarbonate prepared according to the method of this invention presents better thermal stability. For example, for the copolymer of $CO_2$/propylene oxide (PO), the glass transition temperature ($T_g$) is >30° C. However, the $T_g$ of the $CO_2$/PO copolymer prepared using the current technology of double metal complex catalysts is often <10° C. Thus, such $CO_2$/PO copolymer cannot be used as a useful material directly.

Compared to the current technology, this invention has several beneficial technical results as follows:

1) The metal cyanide complex catalyst in this invention contains a special active site in which neutral electron-donating ligands L2 coordinated to $M^1$. At the same time, this catalyst presents very high surface areas for that it owns nano-lamellar and nano-spherical shape and nano-porous structure in the catalyst. As a result, the metal cyanide complex catalyst in this invention is different from the traditional DMC catalysts in composition, structure, active site and shape. This catalyst shows surprising catalytic performance, especially for the aforementioned copolymerization in both high polymerization selectivity and productivity. Therefore, this catalyst overcomes the insufficiency of the traditional DMC catalysts for the copolymerization of epoxides with $CO_2$, anhydrides, esp. for epoxides/$CO_2$ copolymerization.

2) The preparation method for the metal cyanide complex catalyst in this invention, through the coordination of the neutral electron-donating ligand L2 with $M^1$, introduction of L3 acted as macromolecular external complexing agent and template as well as control of pH values of the preparation system to obtain metal cyanide complex catalyst with active sites that are different from traditional DMC and successfully achieves change the aggregation of the catalysts. These measures result in a catalyst with nano-lamellar and nano-spherical shape and nano-porous structure, leading the increase of surface area and productivity. Moreover, a two-preparation step is adopted for preparing metal cyanide complex catalyst of the present invention, which is better than traditional one-step water phase preparation method for DMC catalyst. Thus, the method of the present invention does not require the use of mixed solution of water with large amounts of traditional external organic complexing agents such as tertiary butyl alcohol, tetrahydrofuran and ethylene glycol dimethyl ether and so on, and thus avoided the waste of these organic compounds and pollution to the environment.

3) The metal cyanide complex catalyst of the present invention can be applied to catalyze epoxides homopolymerization and copolymerization of epoxides with $CO_2$ (and/or cyclic anhydride), to prepare polyether, polycarbonate, polyester and poly (carbonate-ester) and exhibits a high productivity and selectivity. Especially, for the epoxides-$CO_2$ copolymerization, this catalyst shows a surprising catalytic effect. In comparison with previous techniques for producing polycarbonate, metal cyanide complex catalyst in this invention can be also applied to catalyze the copolymerization of $CO_2$ with two and more epoxides to make aliphatic polycarbonates with a high alternative degree, high molecular weight and high productivity, and the cyclic carbonate by products content is very low. While most of the catalysts reported in the current technology usually have relatively high stereoselectivity to exposides monomers. This invention easily adjusts the properties of the resultant copolymer by changing the kind and ratio of the epoxides monomers.

4) In the method for preparing aliphatic polycarbonates by using metal cyanide complex catalysts of the present invention, the application of the metal cyanide complex catalysts with new active site in this invention can lead to fully alternating copolymerization of epoxides-$CO_2$ with a high productivity, to produce fully alternative, high molecular weight copolymer with an improved thermal stability and biodegradability. For the alternating copolymerization of $PO/CO_2$ catalyzed by the catalysts of the present invention, the productivity of the catalyst is >1.0 kg polymer/g catalyst, which is significantly higher than those of other heterogeneous catalysts in this field. The high productivity significantly decreases the production cost.

In the copolymerization reaction, under the catalyzing effect of the metal cyanide complex catalysts of the present invention, the reaction process avoided the generation of thermal favorable cyclic carbonate byproduct to a large degree. For the alternating copolymerization of $PO/CO_2$, the content of cyclic carbonate in the crude product is <10%, usually <5%; for the alternating copolymerization of $CHO/CO_2$ and cyclopentene oxide/$CO_2$, no cyclic carbonate byproduct is observed. The weight-average molecular weight of copolymer is >80,000, the molecular weight distribution is 1.2~4. As a result, this invention including preparation the catalyst and the method for preparing polycarbonate have overcome the shortcomings of previous systems. That is, this invention can realize the production of polycarbonate with a high productivity, high molecular weight and alternative degree, as well as a low or even zero production of cyclic carbonate byproduct. These materials have improved thermal stability and biodegradability and thus have potential application in preparing medical materials.

The metal cyanide complex catalyst of the present invention is easy to prepare, not sensitive to water and air. It is a heterogeneous catalyst and thus can be removed from the product and reused. In addition, the method provided by this invention can get polycarbonate with a high productivity, high molecular weight and alternative degree, as well as low production of cyclic carbonate byproduct.

EMBODIMENTS OF THE INVENTION

The present invention is explained in details by reference to drawings and examples. However, the present invention is not limited by these references.

Example 1

Step 1: $K_3Co(CN)_6$ (0.80 g, 0.0024 mol) was dissolved in the solution of de-ionized water I (50 mL) and tertiary butyl alcohol (2 mL, 1.57 g), the obtained mixed solution was denoted as solution I'. The pH value of the solution I' was adjusted to <7 by adding hydrochloric acid that was evenly dissolved until the solution was transparent. $ZnCl_2$ (4.0 g, 0.029 mol) was dissolved in the solution of de-ionized water II (20 mL), which was denoted as solution II'. Solution I' was added to the solution II' at 40° C. under stirring condition. The reaction was agitated for 24 hours. Then the resultant precipitate was separated by pressure filtration, to obtain a semi-dried solid cake.

Step 2: The obtained product and $ZnCl_2$ (0.5 g, 0.0037 mol) were dispersed in anhydrous tertiary butyl alcohol (20 mL) containing N-phenyl-imidazole (2.0 g, 0.0139 mol). The reaction was agitated for 10 hours at 60° C. Then the resultant white precipitate was separated by pressure filtration and reslurried in anhydrous tertiary butyl alcohol (40 mL) at 60° C. for 10 hours, then cooled and filtered. The same procedure was repeated for three times. Finally, the white precipitate was separated and dried at 80° C. under vacuum to a constant weight. 1.3 g of solid metal cyanide complex catalyst was obtained.

The elemental analysis result of the catalyst: Zn: 26.4 wt %; Co: 11.4 wt %; Cl: 2.4 wt %; C: 28.7 wt %; H: 2.10 wt %; N: 21.1 wt %.

SEM photos show the catalyst is nanolamellar, the thickness of lamella is 20~40 nm.

XRD patterns show wide peaks between $2\theta=13$ to $25°$

The average pore diameter is 4 nm according to BET analysis (by $N_2$ absorption and desorption method).

Example 2

The same procedure as Example 1 was carried out, except that the solution I' was added $EO_{20}PO_{70}EO_{20}$ (2.1 g, Pluronic P123, Aldrich), which was 4.2 wt % of the de-ionized water's weight (50 g). Finally, 1.5 g of metal cyanide complex catalyst was obtained.

The elemental analysis result: Zn: 19.4 wt %; Co: 9.6 wt %; Cl: 6.3 wt %; C: 28.84 wt %; H: 3.27 wt %; N: 16.35 wt %

Figure 1:
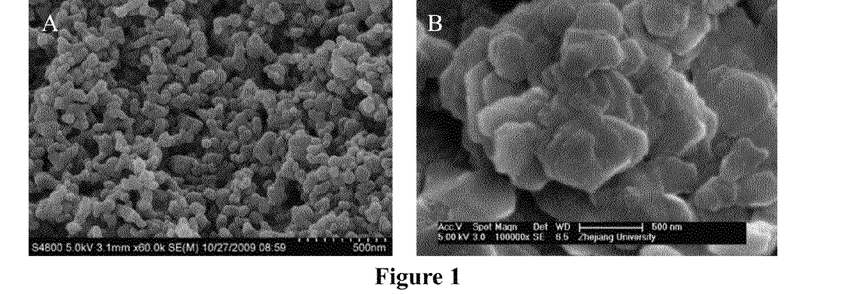
FIG. 1 is the scanning electron microscope (SEM) results of the metal cyanide complex catalysts of the present invention, in which A is the catalyst made for Example 2 and B is the catalyst made for Example 3.

SEM photos (FIG. 1A) show the catalyst is spherical shape, the average size is <100 nm.

Figure 2:
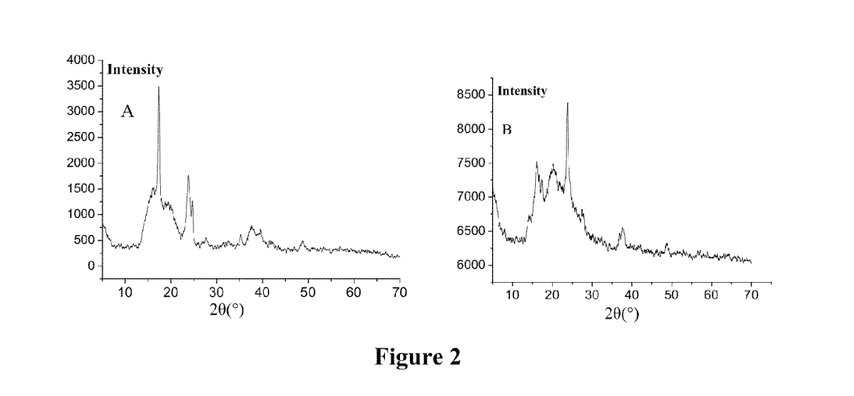
FIG. 2 is the wide angle X-ray diffraction (WAXD) patterns of the metal cyanide complex catalysts of the present invention, in which A is the catalyst made for Example 2 and B is the catalyst made for Example 3.

XRD patterns (FIG. 2A) show wide peaks at $2\theta=13$ to $25°$

The average pore diameter is 8 nm according to BET analysis.

Figure 3:
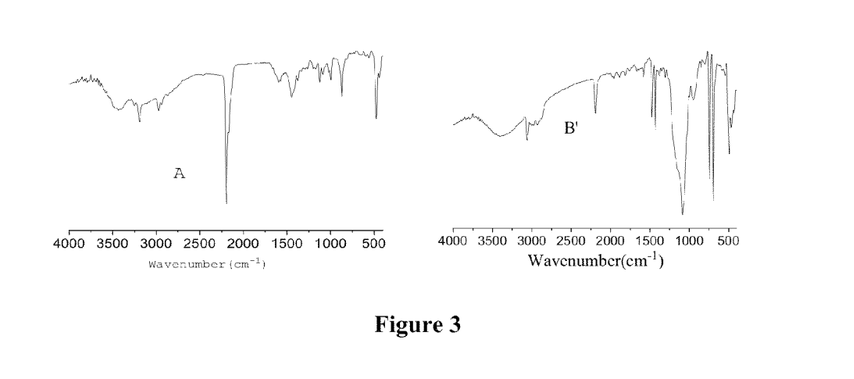
FIG. 3 is the Infrared Spectroscopy results of the metal cyanide complex catalysts of the present invention, in which A is the catalyst made for Example 2 and B' is the catalyst made for Example 5.

FT-IR (FIG. 3A) shows some peaks at 2294 and 472 $cm^{-1}$ which are ascribed to the characteristic peaks of CN and Co—C respectively, the peaks at 1500 and 1200 $cm^{-1}$ suggest that organic complexing agent existed in the catalyst.

Example 3

The same procedure as Example 1 was carried out, wherein the 1-phenyl-imidazole in the step 2 was replaced by equimolar diphenyl sulfoxide, anhydrous tertiary butyl alcohol was replaced by isopyknic anhydrous tetrahydrofuran. Slurry temperature is the refluxing temperature of tetrahydrofuran. Finally, 1.8 g of metal cyanide complex catalyst was obtained.

The elemental analysis result of the catalyst: Zn: 19.2 wt %; Co: 9.2 wt %; Cl: 2.8 wt %; C: 26.04 wt %; H: 1.03 wt %; N: 15.78 wt %.

SEM photos (FIG. 1B) show nanolamellar structure with a thickness of 20~40 nm.

XRD patterns show wide peaks at 2θ=13 to 25°.

The average pore diameter is 45 nm according to BET analysis.

Example 4

The same procedure as Example 1 was carried out, wherein the $ZnCl_2$ (4.0 g) was replaced by zinc acetate (15.0 g), the 1-phenyl-imidazole in step 2 was replaced by equimolar diphenyl acetonitrile, and in step 2, zinc acetate was not used. Finally, 1.5 g of metal cyanide complex catalyst was obtained.

The elemental analysis: Zn: 26.6 wt %; Co: 12.5 wt %; C: 31.45 wt %; H: 1.49 wt %; N: 17.32 wt %.

SEM images show the catalyst shape is spherical with an average size of about 50 nm.

Example 5

Step 1: An amount of $EO_{20}PO_{70}EO_{20}$ (8.0 g) was dissolved in the solution of de-ionized water (60 mL) and tetrahydrofuran (2 mL), when it was agitated to be transparent, an amount of $K_3Co(CN)_6$ (1.0 g, 0.003 mol) was added, it was designated as the mixed solution I'. The pH value of solution I' was adjusted to 4 by adding an appropriate amount of hydrochloric acid under vigorous stirring that was evenly dissolved until the solution was transparent (the ration of $EO_{20}PO_{70}EO_{20}$ to de-ionized water was 13.3%). An amount of $ZnCl_2$ (2.5 g, 0.018 mol) was dissolved in de-ionized water (20 mL) under vigorous stirring (800 rpm), and then 4 g of tetraethyl orthosilicate (TEOS) was added to the $ZnCl_2$ solution. The obtained solution was designated as solution II'. Solution I' was added dropwise to the solution II' at 40° C. under stirring. The reaction was then agitated for 24 hours. Then the resulting semi-dried white precipitated cake was separated by pressure filtration.

Step 2: The obtained white precipitated cake and 0.5 g of $ZnCl_2$ were dispersed in anhydrous tertiary butyl alcohol (50 ml) dissolving an amount of bipyridine (4.5 g, 0.0288 mol). The reaction was performed at the pressure of the system in a sealed autoclave for 10 hours. Then the resulting white precipitated solid was separated by pressure filtration and reslurried in anhydrous tertiary butyl alcohol for three times. Finally, the white precipitated solid was be separated and dried under vacuum to a constant weight. 2.3 g of solid was obtained.

The elemental analysis result: Zn: 23.4 wt %; Co: 7.8 wt %; Cl: 4.2 wt %; C: 36.19 wt %; H: 2.18 wt %; N: 16.63 wt %.

SEM images show the catalyst is irregular flaky with a thickness of 80 nm.

XRD patterns show wide peaks between 2θ=13 to 25°.

The average pore diameter is 32 nm according to BET analysis.

FT-IR spectrum (FIG. 3B') shows the peaks at 2294 and 472 $cm^{-1}$ are ascribed to the characteristic peaks of CN and Co—C respectively, the broad peaks between 1000 and 1300 $cm^{-1}$ suggest that the existence of the silica support from the hydrolization of TEOS and a few residual polyether.

Example 6

The same procedure as Example 5 was carried out, wherein the $K_3[Co(CN)_6]$ was replaced by $K_2Ni(CN)_4$ (0.0033 mol), a $SiO_2$ supported Zn—Ni catalyst was obtained with an amount of 1.6 g.

The elemental analysis result: $SiO_2$: 22.3%; Zn: 16.5 wt %; Ni: 3.8 wt %; Cl: 3.5 wt %; C: 25.73 wt %; H: 1.39 wt %; N: 16.86 wt %.

SEM images show the shape of the catalyst is irregular lamella with an average thickness of less than 100 nm.

Example 7

The same procedure as Example 6 was carried out, wherein the $K_3Co(CN)_6$ was replaced by equimolar $K_3[Co(CN)_5Br]$, the bipyridyl was replaced by hexaphenyltriphosphazene (1.7 g, 0.0024 mol). According to the method of Example 6, 2.5 g of catalyst carried by SiO2 and containing different internal complexing agents was obtained.

The elemental analysis result of the catalyst: Zn: 20.4 wt %; Co: 7.6 wt %; Cl: 4.3 wt %; Br: 4.5 wt %; C: 32.68 wt %; H: 2.09 wt %; N: 16.25 wt %.

SEM images show the shape of the catalyst is spherical with an average thickness of less than 100 nm.

The average pore diameter is 60 nm according to BET analysis.

In the above analysis method, the elemental analysis was determined by X-ray fluorescence spectrometry, atomic spectrometry and CHN elemental analysis. The pore structure of the catalyst was measured by the BET method ($N_2$ absorption and desorption). Before BET test, the organic components in the catalyst should be removed thoroughly. This can be achieved by calcination below 350° C. (a majority of the organic components were decomposed, but the backbone of the catalyst would not be destroyed because the catalyst decompose above 400° C.), or by extraction repeatedly through using strong polar solvents below 200° C. The BET curves and TEM results showed that the nano-pore structure was produced by accumulation of nano-lamellar and spherical catalyst and was thus irregular.

In the following examples, the molecular weight and its distribution were determined by gel permeation chromatography (GPC), using polystyrene as the standard for calibration, using tetrahydrofuran as the flow phase and measured at 35° C. The alternative degree of polymer and content of cyclic carbonate were calculated from $^1$HNMR. Catalytic activity was measured by product weight and the glass transition temperature of polymer was determined by the second thermal analysis curve with a heating process of 10° C./min.

Example 8

12 mg of catalyst (5 and 15 mg catalyst were used in Table 1, Nos. 2 and 3) was added into a clean autoclave, dried under vacuum at 80° C. for 24 hours, then cooled to room temperature. 30 mL of dried propylene oxide (PO) was injected into the autoclave using a syringe under negative pressure. $CO_2$ was pressed into the autoclave under stirring condition. The reactor was then heated to a desired temperature (30-100° C.) and pressured to 2.5-7.0 MPa. The reaction was carried out for 10 h and then cooled. After extra gas was released in the reactor, then the product was removed for $^1$HNMR and GPC analysis to determine polymer structure and weighing to calculate productivity. Catalytic activity was noted as the produced polymer (g) per g catalyst. The different polymerization reaction and polymerization products structure information are listed in Table 1 below.

TABLE 1

PO—CO$_2$ copolymerization catalyzed by various metal cyanide complex catalysts

| No. | catalyst | temperature (° C.) | pressure (MPa) | Content of cPC (%) | catalytic activity | alternative degree | Mw (10$^{-4}$) | PDI |
|---|---|---|---|---|---|---|---|---|
| 1 | Ex. 1 | 60 | 5.0 | 3.5 | 1950 | 94.8 | 16.4 | 1.9 |
| 2 | Ex. 1 | 60 | 4.0 | 4.6 | 1800 | 95.0 | 11.4 | 2.3 |
| 3 | Ex. 1 | 60 | 7.0 | 2.3 | 1650 | 97.8 | 23.9 | 2.0 |
| 4 | Ex. 2 | 60 | 4.0 | 5.3 | 2150 | 92.4 | 9.1 | 2.0 |
| 5 | Ex. 3 | 45 | 2.5 | 2.7 | 1885 | 97.5 | 10.1 | 1.8 |
| 6 | Ex. 4 | 60 | 4.0 | 3.6 | 1250 | 96.3 | 11.0 | 2.1 |
| 7 | Ex. 5 | 70 | 5.0 | 3.0 | 2350 | 92.5 | 8.1 | 1.7 |
| 8 | Ex. 6 | 60 | 5.0 | 3.5 | 1117 | 96.8 | 11.4 | 1.9 |
| 9 | Ex. 7 | 60 | 5.0 | 4.2 | 1300 | 93.8 | 13.5 | 2.1 |

Figure 4:
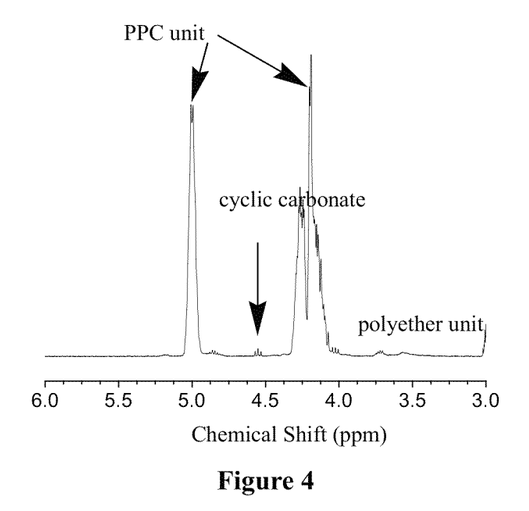
FIG. 4 is the nuclear magnetic resonance spectra of the $CO_2$/epoxide coperlymerization product (crude product) catalyzed (Table 1, No. 3) by the catalyst made according to Example 1 of the present invention.

The glass transition temperatures ($T_g$s) of the produced polycarbonate in the Nos. 1-8 were >30° C. $M_w$ of Polycarbonate of No. 3 was up to 239 kDa, the corresponding $^1$HNMR spectrum of this crude polycarbonate was shown in FIG. 4(left). The chemical shifts at 4.9 ppm and 4.0-4.3 ppm are ascribed to the methine and methylene protons of carbonate units, while 4.5 ppm and 3.5-3.7 ppm were ascribed to the methine protons of cyclic carbonate and methylene and methine protons of ether unit, respectively. It is seen that the content of cyclic carbonate and polyether were rather low. $T_g$ curve of the polycarbonate of No. 3 is in curve 1 in FIG. 6 and is 34.3° C.

Example 9

The prepared catalysts from Examples 1, 2 and 5 were employed to catalyze the copolymerization of cyclohexene oxide (CHO) or 4-vinyl cyclohexene oxide (VCHO) with CO$_2$.

Prior to polymerization reaction, a 500-mL autoclave was heated to 60~80° C. for 1 hour for removing trace water, then 20 mg catalyst was added into the autoclave. 40 mL of CHO (or 40 mL of VCHO) or 40 ml tetrahydrofuran was injected into the autoclave. The reactor was then heated and pressured to the desired temperature and pressure. The reaction was carried out for 10 h. After the reaction, the autoclave was cooled down, the pressure was vented and the product was removed. The product was placed under vacuum for drying at 60° C. to remove non-reacted monomers. To further purify the product, it can be dissolved by methylene dichloride (CH$_2$Cl$_2$) then precipitated by methanol. In the Example No. 12 of Table 2, 20 mL CHO and 20 mL tetrahydrofuran were used and 24 h was the reaction time. The reaction condition, amounts of reactants and products structure information are listed in Table 2.

TABLE 2

The copolymerization of CHO—CO$_2$ and VCHO—CO$_2$

| No. | catalyst | epoxide/ volume (mL) | temperature (° C.) | pressure (MPa) | Mw (10$^{-4}$) | PDT | catalytic activity | alternative degree |
|---|---|---|---|---|---|---|---|---|
| 10 | Ex. 1 | CHO/40 | 80 | 3.8 | 14.0 | 2.1 | 2350 | 97.0 |
| 11 | Ex. 1 | VCHO/40 | 70 | 3.8 | 13.9 | 2.2 | 2100 | 99.0 |
| 12 | Ex. 2 | CHO/40 | 70 | 5.0 | 15.6 | 1.8 | 2500 | 99.0 |
| 13 | Ex. 5 | CHO/40 | 70 | 3.8 | 13.3 | 1.9 | 2000 | 94.0 |

The $T_g$s of the produced copolymers in Table 2 are greater than 108° C. (DSC, 10° C./min from second heating curve).

Example 10

The catalyst prepared from Example 3 was employed to catalyze two different expoxides terpolymerization with CO$_2$.

Prior to polymerization reaction, a 500-mL autoclave was heated to 60~80° C. for 1 h for removing trace water, then 15 mg catalyst (catalyst made according to Example 3) was added to the autoclave. A mixture of two epoxides monomers in a certain ration was injected into the autoclave, stirred to raise the temperature to a certain degree and CO$_2$ was added to increase the pressure to a certain pressure. After reaction for 10-15 hours, the autoclave was rapidly cooled down and the pressure was vented. The product was removed and placed under vacuum at 60° C. to dry in order to remove unreacted monomers. To further purify the product, it was dissolved into methylene dichloride and precipitated by methanol. The reaction condition, amounts of reactants and products structure information are listed in Table 3.

TABLE 3

The terpolymerization of two epoxides and CO2

| No. | temperature (° C.) | pressure (MPa) | epoxide 1 (mL) | epoxide 2 (mL) | catalytic activity | content of cPC (%) | alternative degree | $M_w$ ($10^{-4}$) | PDI |
|---|---|---|---|---|---|---|---|---|---|
| 15 | 75 | 4.0 | CHO/5 | VCHO/15 | 1230 | 0 | 94.4 | 13.5 | 2.5 |
| 16 | 50 | 5.0 | CHO/5 | PO/45 | 1400 | <2 | 91.8 | 8.5 | 2.0 |
| 17 | 60 | 4.0 | CHO/7 | PO/60 | 1550 | <2 | 95.0 | 10.5 | 1.9 |
| 18 | 70 | 4.0 | CHO/7 | PO/60 | 1300 | <2 | 93.0 | 8.5 | 2.2 |
| 19 | 50 | 4.0 | CHO/10 | PO/60 | 1344 | <1 | 94.0 | 10.9 | 2.2 |
| 20 | 50 | 6.0 | CHO/7 | PO/60 | 1480 | <1 | 98.0 | 20.6 | 2.4 |

Figure 5:
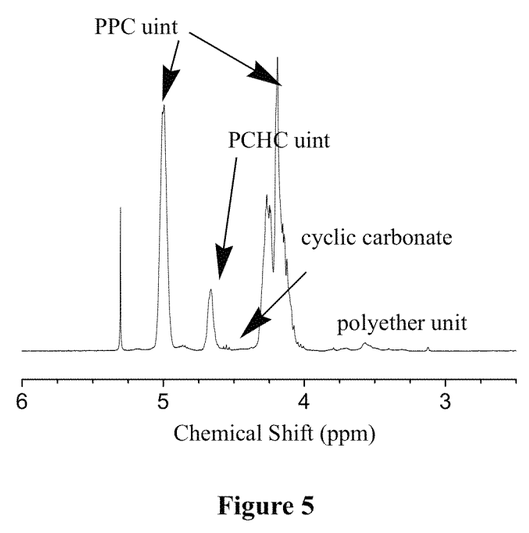
FIG. 5 is the nuclear magnetic resonance spectra of the $CO_2$/epoxide/CHO coperlymerization product (crude product) catalyzed (Table 3, No. 20) by the catalyst made according to Example 3 of the present invention.
Figure 6:
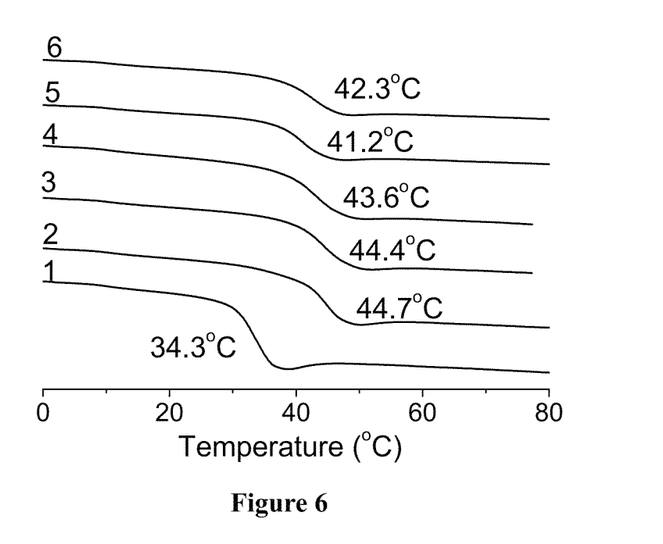
FIG. 6 shows glass transition temperatures of different polymers made through catalyzation according to the methods of the present invention. Curve 1 shows glass transition temperature of the copolymer product made from epoxides and $CO_2$ of Table 1 No. 3. Curves 2-6 show glass transition temperatures of the polymers of Table 3, Nos. 16, 17, 18, 19 and 20, respectively.

$T_g$s of Nos. 16, 17, 18, 19 and 20 in Table 3 are 42.3° C., 41.2° C., 43.6° C., 44.4° C. and 44.7° C., respectively (DSC method, 10° C./min, taken from the thermal transition of the second curve), see curves 2~6 in FIG. 6. $^1$HNMR spectrum of the crude terpolymer of $CO_2$/PO/CHO in No. 20 was shown in FIG. 5. The chemical shifts at 4.9 ppm and 4.4 ppm are ascribed to the methine and methylene protons of propylene carbonate unit and cyclohexene carbonate unit, while 4.5 ppm and 3.5~3.7 ppm are ascribed to the methine protons of cyclic carbonate and methylene and methine protons of ether unit, respectively. As shown in Table 1, the intensity of peaks at 4.5 ppm and 3.5~3.7 ppm is rather low, suggesting the contents of cyclic carbonate byproduct and polyether in the crude product was also rather low.

Example 11

The catalyst employed in this example was prepared according to Example 1. Step polymerization was adopted for epoxides homopolymerization in this example.

7.0 mg of catalyst and 20 g of starting material (PPG-400) were added into a 500-mL stainless steel autoclave reactor, then the reactor was heated to 110° C. and $N_2$-vacuum cycle was carried out repeatedly for removing the trace water for 0.5 hours. After the autoclave was further heated to 120° C., PO (10 mL) was injected into autoclave using a metering pump. After the pressure of the system decreased dramatically (18 minutes), PO monomer (100 mL) was injected into autoclave in batches with 10 mL PO for each time within 5 h. After the reaction, the pressure was reduced to remove the remaining monomer. A viscous liquid product was then obtained.

$M_n$=3.8 kDa, PDI=1.08. The percentage of the product with $M_n$>100 kDa in the final product was below 500 ppm, while those of PO ROP catalyzed by traditional DMC catalyst was generally >1000 ppm.

The catalytic activity was 51.5 kg polyether/g catalyst.

Example 12

The catalyst employed in this example was prepared according to Example 4. The catalyst was adopted for epoxides/anhydride copolymerization in this example.

Prior to polymerization reaction, a 60-mL autoclave was dried under vacuum at 110° C. for 2 hours for removing trace water, and cooled to room temperature in the drying tower. 3.0 mg of the catalyst, 2.0 g of maleic anhydride, 4 mL of cyclohexene oxide and 4.0 mL of tetrahydrofuran were added into the autoclave. The reactor was sealed and then heated in an oil bath to a temperature of 90° C. for reaction for 5 hours with magnetic stirring. After the reaction, the autoclave was rapidly cooled down and the pressure was vented. Crude product was removed. The pressure was reduced and solvents were removed, then the crude product was solved in THF and precipitated by methanol, then dried under vacuum to obtain a yellow product, which was weighed to calculate the conversion. The content of polyether unit and polyester unit was calculated from $^1$HNMR spectrum.

$M_n$=24,000, PDI=1.6. Alternative degree: 96%. The final catalytic activity was 3.2 kg polyether/g catalyst. The glass transition temperature is 82° C.

Example 13

The catalyst employed in this example was prepared according to Example 4. The catalyst was adopted for epoxides/anhydride/$CO_2$ terpolymerization in this example.

Prior to polymerization reaction, a 100-mL autoclave was dried under vacuum at 110° C. for 2 hours for removing trace water. 10.0 mg of catalyst, 4.0 g of maleic anhydride, 40 mL of cyclohexene oxide and 40 mL of tetrahydrofuran were sequentially added into the autoclave. The reactor was sealed. $CO_2$ was added to a desired pressure of 4.0 MPa. The reaction was performed for 5 h with stirring. After the reaction, the autoclave was rapidly cooled down and pressure was vented. Crude products were removed. The products were dissolved with methylene dichloride and precipitated by methanol, then the yellow products were dried under vacuum. The conversion was calculated from weight of the products. The content of polyether unit and polyester unit was calculated from $^1$HNMR spectrum.

$M_n$=30,000, PDI=1.8. Alternative degree was 98%. The final catalytic activity was 5.6 kg polyether/g catalyst. The glass transition temperature is 108° C.

The invention claimed is:

1. A process for preparing a metal cyanide complex catalysts comprising the following steps:
   step 1: a solution I' is prepared by mixing a cyanide metal salt of formula (2) into a mixture of L3, de-ionized water I, alcohol and/or ether solvents, and the pH value of the solution I' is then adjusted to less than 7.0; a solution II' is comprised of $M^1(X)_g$ salt, Su or Su precursors, de-ionized water II; the solution I' and the solution II' are then mixed by adding the solution I' into the solution II' under stirring at 0~120° C. for 0.5~200 hour, the resultant precipitate is separated and dried, $$M^3_e[M^2(CN)_b L1_c]_f \quad (2)$$

wherein, $M^3$ is an alkali metal ion, alkali earth metal ion or hydrogen ion, e and f are positive numbers, $M^2$, L1, b, and c are the same as (1) described below,
wherein, L3, $M^1$, X and Su are the same as in formula (1), g is 1 or 2,
in the mixed solution I', molar ratio of the cyanide metal salt of formula (2) and de-ionized water I is 0.005-2 g/mL, the weight ratio of L3 and de-ionized water I is 0~40%, the volume fraction of alcohol and/or ether with the de-ionized water I is 0~2, in the mixed solution II", molar ratio of $M^1(X)_g$ salt/de-ionized water II is 0.05~1 g/1 mL, molar ratio of the cyanide metal salt of formula (2)/$M^1(X)_g$ salt is 1/1~50, mass ratio of the cyanide metal salt of formula (2) and Su (or Su precursor) is 1/0~20, step 2: solid product prepared from step 1 is dissolved and reslurried in an anhydrous organic solvent containing L2 for several times, molar ratio of L2/the cyanide metal salt of formula (2) is 0.1~10, slurry temperature is 20~120° C., and slurry time is 0.5~200 h, slurry action being under an inert atmosphere or closed reactive vessel, then the metal cyanide complex catalyst is obtained by a distillation, separation and drying processes; wherein the metal cyanide complex catalyst has the formula:

(1)

$$M^1{}_a[M^2(CN)_b L1_c]_d(X)_m(L2)_n \cdot x Su \cdot y L3 \cdot z H_2O \quad (1)$$

wherein, $M^1$ is a divalent metal ion, which is selected from one of $Zn^{2+}$, $Co^{2+}$, $Ni^{2+}$ or $Fe^{2+}$;

$M^2$ is a divalent or trivalent metal ion (not including $Fe^{2+}$ or $Fe^{3+}$), which is selected from one of $Co^{3+}$, $Ni^{2+}$, $Cd^{2+}$, $Cr^{3+}$ or $Mn^{3+}$;

L1 is an internal ligand which coordinates with $M^2$, it is selected from one or two of mono-dentate ligands with N, O, P or S as a coordinate atom, bi-dentate ligands with O, S, P or N as a coordinate atom or halide anions;

X is an anion selected from one or more of $F^-$, $Cl^-$, $Br^-$, $I^-$, $OAc^-$, $SO_4^{2-}$, $NO_3^-$, aryloxy anions, and organic carboxylic ions;

L2 is an electron-donating neutral ligand with N, O, P and S as a coordinated atom, and coordinated with $M^1$;

Su is selected from one or more of halides, sulfates and nitrates of the IIA and IIIA group metal elements, lithium halide salts, silicon dioxide, titanium dioxide;

L3 is a water-soluble polymer, a polymer that can self-assembly in a mixed solution of water and alcohol, or a mixed solution of water and ether, or a mixed solution of water, alcohol and ether;

a and d are positive numbers, b is positive integer, c is 0, 1 or 2, m and n are positive numbers, x, y and z are zero or positive numbers, and a:d=1~4, a:n=0.001~5.

2. The process according to claim 1, wherein molar ratio of the cyanide metal salt of formula (2)/$M^1(X)_g$ salt is 1/1~30 in step 1.

3. The process according to claim 1, wherein the volume fraction of alcohol and/or ether with the de-ionized water I in mixed solution I' is 0~0.8 in step 1.

4. The process according to claim 1, wherein the slurry temperature is 40~100° C. in step 2.

5. The process according to claim 1, wherein in step 2, the anhydrous organic solvent containing L2 and $M^1(X)_g$ salt, the molar ratio of $M^1(X)_g$ salt to cyanide metal salt of formula (2) is 0~2.

6. The metal cyanide complex catalysts are described according to claim 1, wherein the electron-donating neutral ligand L2 is selected from the group consisting of N-alkyl imidazoles, N-aryl imidazoles, bipyridyl, pyridine, aliphatic nitriles, aromatic nitriles, N,N'-dialkyl amides, N,N'-diaryl amides, N-substituted cyclic amides, sulfoxide or sulfone compounds, organic carboxylates, ketones, cyclic ketones, phosphates, all alkyl-substituted cyclotriphosphazenes, full-aryl-substituted cyclotriphosphazenes, carbonates, cyclic lactones, thioethers, cyclic carbonates or cyclic ethers.

7. The metal cyanide complex catalysts are described according to claim 1, wherein their shape is nano lamellar or nano spherical, and they have nanopores with an average diameter of less than 100 nm.

* * * * *